US005403582A

United States Patent [19]

Nazerian et al.

[11] Patent Number: 5,403,582

[45] Date of Patent: Apr. 4, 1995

[54] VACCINE COMPRISING FOWLPOX VIRUS RECOMBINANTS EXPRESSING THE ENVELOPE GLYCOPROTEIN OF AN AVIAN RETICULOENDOTHELIOSIS RETROVIRUS

[75] Inventors: Keyvan Nazerian, Haslett; Jay G. Calvert, Lansing; Richard L. Witter, Okemos; Noboru Yanagida, East Lansing, all of Mich.

[73] Assignees: Nippon Zeon Co., Ltd., Tokyo, Japan; The United States of America as represented by the Secretary of Agriculture, Washington, D.C.

[21] Appl. No.: 7,282

[22] Filed: Jan. 21, 1993

[51] Int. Cl.$^6$ ........................ A61K 39/21; C12N 15/48

[52] U.S. Cl. .............................. 424/207.1; 424/199.1; 435/69.3; 435/172.3; 435/235.1

[58] Field of Search .............. 424/88, 89, 93 A, 207.1, 424/199.1; 935/32; 435/172.3, 69.3, 252.3

[56] References Cited

U.S. PATENT DOCUMENTS 5,174,993 12/1992 Paoletti ................................ 424/89
5,187,087 2/1993 Sondermeijer et al. ......... 435/172.1
5,208,024 3/1993 Van Den Bosch .................. 424/92

OTHER PUBLICATIONS

Federspiel et al, Virology 173(1): 167–177, 1989.
Witter et al, Avian Diseases 33:226–235, 1989.
Earl et al, Science 234:728–731, 1986.
Fadly et al, Infection and Immunity 37(3):1156–1161, 1982.
Bennett et al, Virus Res 8(1) pp. 73–77, 1987.

*Primary Examiner*—Christine M. Nucker
*Assistant Examiner*—Julie Krsek-Staples
*Attorney, Agent, or Firm*—Birch, Stewart, Kolasch & Birch

[57] ABSTRACT

A recombinant fowlpox virus is provided which is useful as a vaccine for protection against avian reticuloendo-theliosis virus-associated diseases. In a specific embodiment, the recombinant virus expresses a gene encoding an envelope glycoprotein of spleen necrosis virus under the control of a poxvirus promoter, inserted in a nonessential region of the fowlpox virus genome.

17 Claims, 6 Drawing Sheets

VACCINE COMPRISING FOWLPOX VIRUS RECOMBINANTS EXPRESSING THE ENVELOPE GLYCOPROTEIN OF AN AVIAN RETICULOENDOTHELIOSIS RETROVIRUS

BACKGROUND OF THE INVENTION

1. Field of the Invention

The present invention relates to a recombinant fowlpox virus and vaccine containing said virus that is useful in protecting poultry against avian reticuloendotheliosis retrovirus-induced diseases.

2. Description of Related Art

The reticuloendotheliosis viruses (REVs) are a group of oncogenic and immunodepressive type C avian retroviruses (52). They are distinct from the avian leukosis/sarcoma virus group (21), and are more closely related to mammalian retroviruses, both antigenically (2,47,48) and at the genome level (26,37). Nondefective strains of REV include REV-A, spleen necrosis virus (SNV), chicken syncytial virus (CSV), duck infectious anemia virus, and a number of other isolates (12). These nondefective REVs cause a runting disease syndrome, characterized by splenomegaly, necrosis of the spleen and liver, nerve lesions, and lymphomas of B cell or T cell type in chickens. A single replication-defective, acutely transforming REV isolate is known (REV-T), which carries the rel oncogene and which requires a nondefective helper virus (such as strain REV-A) for replication. REV-T causes an acute reticulum cell neoplasia in inoculated chickens. REVs are known to cause economically important immunodepression in infected chickens, and have been found as contaminants of Marek's disease (20,57) and fowlpox (5) vaccines. REV is associated with sporadic outbreaks of chronic neoplastic disease in turkeys and can cause significant losses in commercial turkey flocks (52,55).

Recombinant DNA technology has allowed the construction of recombinant vaccines that contain only those desired viral genes or gene products that induce immunity without exposing the animal to genes that may induce pathological disorders. Pox viruses, including Avipoxvirus, especially the fowlpox virus (FPV), provide excellent models for such vaccines. These viruses have a large DNA molecule with numerous nonessential regions that allow the insertion of several immunogenic genes into the same virus for the purpose of creating multivalent vaccines. These multivalent vaccines may induce cell-mediated as well as antibody-mediated immune response in a vaccinated host.

No vaccine for REV is currently available. Although accurate data on the economic significance of REV-associated diseases is not available, the oncogenic potential of these viruses, their ability to cause immunodepression, and their presence as contaminants in poultry biologics justifies research in this area and development of a suitable vaccine.

The envelope glycoproteins of retroviruses (encoded by the env genes) are known to be associated with virus neutralization. The various strains of REV are antigenically very similar (12), suggesting that a live vaccine expressing the env gene of a single REV isolate may provide protective immunity against numerous REV-associated diseases in poultry. The genomes of SNV and REV-A have been molecularly cloned (11,34). Sequence analysis of the env genes of these viruses shows that they are 92.7% identical to each other at the amino acid level, and about 40–50% identical to the env genes of type D and some type C simian retroviruses, with which they share a receptor (22,23).

The poxviruses, due to their high capacity for accepting foreign DNA and their cytoplasmic replication site, have attracted much attention in recent years as vectors for the expression of foreign genes, and for the construction of potential vaccines against animal diseases (6,40). Most of this attention has focused on vaccinia virus, the prototype of the genus Orthopoxvirus (19,27,30), because of its wide host range and relatively well defined molecular biology (18,29).

The Avipoxvirus genus has a host range which is restricted to avian species. Attenuated vaccine strains of these viruses are commercially available (46). Avipoxviruses show promise not only as safe vectors for the construction of live recombinant poultry vaccines, but also as vectors for replication-defective mammalian vaccines (42,43,45,50). Fowlpox virus (FPV), the prototype of this genus, has been used successfully as a recombinant vaccine to immunize chickens against several diseases, including Newcastle disease virus (7,8,17,25,36,41), avian influenza (4,9,44), Marek's disease virus (32,56), and infectious bursal disease virus (3).

SUMMARY OF THE INVENTION

The present inventors have inserted the env gene of SNV (22), shown in the Sequence Listing as SEQ.ID No.:1, under the control of either $P_{7.5}$ or a strong synthetic poxvirus promoter, into either of two nonessential positions in the FPV genome, in both possible orientations. Of these eight recombinants, the four which employed the synthetic promoter gave high levels of envelope glycoprotein expression by immunofluorescence. Some of these recombinant FPVs were also tested in vivo, and were found to elicit neutralizing antibodies in chickens. One of the recombinants, f29R-SNenv, was used to immunize chickens against a challenge with SNV, and was found to reduce viremia titers by several logs, to undetectable levels.

These recombinant FPVs should prove useful as vaccines in the protection of domestic poultry flocks against REV-induced diseases.

Accordingly, it is an object of the present invention to provide an Avipoxvirus that expresses a gene (SEQ. ID No.:1) encoding a protein (SEQ. ID No.:2) of an avian retrovirus. Said Avipoxvirus can be a fowlpox virus, and said avian retrovirus can be an avian reticuloendotheliosis retrovirus such as, for example, a spleen necrosis virus. Said Avipoxvirus can also be pigeon poxvirus, turkey poxvirus, quail poxvirus, and canary poxvirus. Said gene can encode an envelope glycoprotein of said avian retrovirus, or can be a gag or pol gene.

It is another object of the present invention to provide a novel, effective, and safe vaccine, available in cell-free form, comprising an anti-avian retrovirus effective amount of said Avipoxvirus, and a pharmaceutically acceptable carrier. This vaccine induces effective immunity against avian reticuloendotheliosis retroviruses.

Another object of the present invention is to provide a cell-free vaccine against avian reticuloendotheliosis retroviruses containing recombinant (rec) FPV that can be lyophilized, stored, and used under normal conditions. For example, the vaccine of the present invention, after lyophilization, can be stored, handled, and transported at ambient temperature (20°–22° C.) and stored at 4° C. for prolonged periods of time. The vaccine can also be stored in a frozen state wherein the cell-free recombinant virus is present in an aqueous solution which is frozen and stored at, for example, −20° C. or −70° C.

Yet another object of the present invention is to provide a method for immunizing poultry against avian reticuloendotheliosis retrovirus-associated diseases, comprising administering to said poultry, including, for example, chickens, ducks, turkeys, geese, quail, etc., said vaccine.

A still further object of the present invention is to provide a method for producing passive protection against avian reticuloendotheliosis retrovirus-associated diseases in poultry progeny, comprising administering to poultry breeder stock said vaccine, thereby producing passive protection in said poultry progeny during the first weeks of life.

Further scope of the applicability of the present invention will become apparent from the detailed description and drawings provided below. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed descriptions taken in conjunction with the accompanying drawings, all of which are given by way of illustration only and are not limitative of the present invention, in which.

DETAILED DESCRIPTION OF THE INVENTION

The following detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The contents of each of the references cited in the present application are herein incorporated by reference in their entirety.

DEFINITIONS

The following definitions are provided to aid the reader in understanding the following description of the present invention:

CEF Cells: chick embryo fibroblast cells.

CSV: chicken syncytial virus; a nondefective strain of REV.

env genes: genes encoding the envelope glycoproteins of retroviruses; associated with virus neutralization.

FPV: fowlpox virus; an Avipoxvirus, the host range of which is restricted to avian species.

PPV: pigeon pox virus.

REVs: reticuloendotheliosis viruses; a group of oncogenic and immunodepressive type C avian retroviruses.

REV-A: a nondefective strain of REV.

REV-T: a replication-defective, acutely transforming REV isolate.

SNV: spleen necrosis virus; a nondefective strain of REV.

MATERIALS AND METHODS

Cells, viruses, plasmids, and monoclonal antibodies

Primary Chick Embryo Fibroblast (CEF) cells were prepared from 11-day-old RPRL line 0 white leghorn embryos using the method of Solomon (39). CEF were grown in Leibovitz-McCoy medium supplemented with 4% calf serum and antibiotics ("medium").

A large plaque variant of FPV(31), isolated from a vaccine strain (CEVA Laboratories) obtained from Dr. Roland W. Winterfield (Purdue University, W. Lafayette, IN), was used in the construction of recombinants. Two randomly selected nonessential DNA fragments from the NP vaccine strain (Shionogi & Co. Ltd., Shiga, Japan) of pigeon pox virus (PPV), were employed in the construction of plasmid transfer vectors. Homologous recombination between PPV plasmids and FPV occurred readily, since the two viruses are very closely related. The restriction enzyme cleavage patterns of PPV are similar to those of FPV(36,38), and sequencing of over 5 kb of homologous DNA indicates that PPV and FPV genes are about 99.9% identical.

The SNV, REV-T(F), and CSV strains of REV (12,52) were used for antiserum induction, neutralization assays, immunoprecipitation experiments, and/or bird challenges.

Plasmid pPB101, which contains the complete provirus of the SNV strain of REV cloned into pBR322 (1), was a generous gift from Dr. Howard M. Temin (McArdle Laboratory, University of Wisconsin, Madison, Wis.).

Monoclonal antibodies 11A25 and 11B118 (13), prepared against REV strain T(C), were kindly provided by Dr. Lucy F. Lee (USDA-ARS Avian Disease and Oncology Laboratory, East Lansing, Mich.).

EXAMPLE 1

Construction of plasmid vectors

Figure 1:
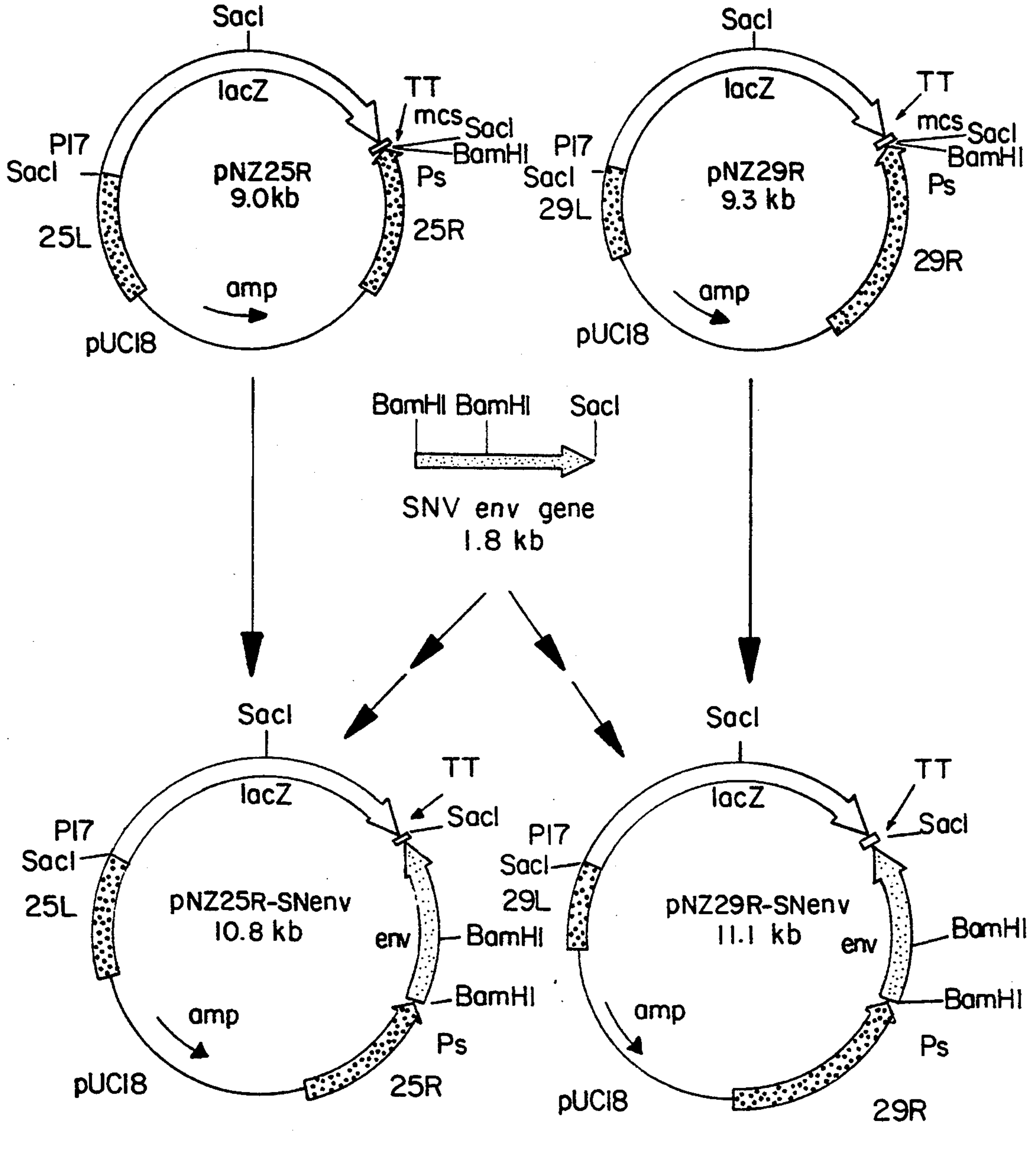
FIG. 1 shows the construction of plasmid vectors for recombination into FPV. The env gene of SNV (SEQ. ID No.:1) was excised from pPB101 (1) by complete digestion with SacI and partial digestion with BamHI. The 1829 bp fragment was cloned, in a two-step procedure, into eight plasmid vectors as described in Materials & Methods. Two of these plasmids (pNZ25R and pNZ29R) are shown here. The resulting chimeric plasmids (pNZ25R-SNenv and pNZ29R-SNenv) were used to construct recombinant FPVs. Abbreviations are as follows: lacZ, *E. coli* β-galactosidase gene; amp, ampicillin resistance gene from pUC18; env, SNV envelope glycoprotein gene; TT, synthetic bidirectional poxvirus early transcriptional terminator; mcs, multiple cloning site; $P_s$, synthetic strong late/early poxvirus promoter; $P_{17}$, a moderately weak FPV early promoter; 25R, 25L, 29R, 29L, the right (R) and left (L) arms of poxvirus DNA flanking the nonessential sites 25 and 29.

A 1829 bp BamHI-SacI fragment of pPB101, which contains the entire open reading frame for the SNV envelope glycoprotein as well as 46 upstream and 41 downstream nucleotides, was initially cloned into a small adaptor plasmid and subsequently into eight related insertion vectors (designated pNZ29R, pNZ29L, pNZ25R, pNZ25L, $pNZ_{7.5}29R$, $pNZ_{7.5}29L$, $pNZ_{7.5}25R$, and $pNZ_{7.5}25L$) for recombination into FPV (FIG. 1). The construction of pNZ29R, which directs the insertion of foreign genes, driven by a synthetic strong late/early pox promoter($P_s$), into a nonessential site of the FPV genome designated position 29, has been described (56). A different nonessential site, designated position 25 (35), is targeted by pNZ25R and other "25" plasmids. The orientation of the inserted foreign gene/lacZ cassette is reversed in pNZ29L and other "L" plasmids, relative to surrounding FPV sequences. Plasmids which contain the "7.5" designation use the vaccinia virus $P_{7.5}$ promoter (rather than the $P_s$ synthetic promoter) to drive expression of the foreign gene.

EXAMPLE 2

Generation and purification of recombinant FPV

CEF monolayers (~$1\times10^7$ cells) were infected with FPV at an moi of 0.1 and incubated for 5 h in serum-free medium. Cells were trypsinized, washed twice in Saline G (0.14M NaCl, 5 mM KCl, 1.1 mM $Na_2HPO_4$, 1.5 mM $KH_2PO_4$,0.5 mM $MgCl_2$, and 0.011% glucose), and resuspended in 0.7 ml Saline G. This cell suspension was mixed with 10 μg of CsCl-purified transfer vector DNA in 0.1 ml of Saline G and subjected to electroporation at 300 V (750 V/cm), 330 μF, low Ω, using a Cell-Porator™ apparatus (GIBCO BRL, Gaithersburg, Md.). After 10 min, transfected cells were plated onto a single 60 mm culture dish and incubated at 37° C. After 3 days, these cells were harvested by scraping and disrupted by sonication to release progeny virus.

Recombinant FPVs were identified and purified using a modification of the method described in Dhawale et al. (16). Briefly, dilutions of the cell lysates were assayed on CEF with an overlay of medium containing 0.8% Bacto agar and lacking phenol red pH indicator. Total plaques were counted after 5–7 days. Recombinants, which expressed the lacZ gene, were identified by staining with 5 ml of a second agar overlay which contained 1 mg/ml Bluo-gal (GIBCO BRL, Gaithersburg, Md.) and lacked serum. Blue plaques became apparent after 1–3 days. Several blue plaques were picked into a small volume of medium, disrupted by sonication, and used to infect the next round of cultures. Plaque purification was continued until only blue plaques were detected.

Recombinant viruses were named according to the transfer vector used (for example, the recombinant virus f29R-SNenv was constructed using the plasmid pNZ29R-SNenv). The structural characteristics of the eight FPV recombinants are shown in Table 1.

TABLE 1

Detection of SNV envelope glycoprotein in recombinant FPV-infected cells by immunofluorescence[a]

| Virus | Genomic Position | Orientation | Promoter | Fluorescence Intensity |
|---|---|---|---|---|
| $f_{7.5}29R$-SNenv | 29 | Right | $P_{7.5}$ | + |
| $f_{7.5}29L$-SNenv | 29 | Left | $P_{7.5}$ | + |
| $f_{7.5}25R$-SNenv | 25 | Right | $P_{7.5}$ | + |
| $f_{7.5}25L$-SNenv | 25 | Left | $P_{7.5}$ | + |
| f29R-SNenv | 29 | Right | $P_s$ | ++++ |
| f29L-SNenv | 29 | Left | $P_s$ | ++++ |
| f25R-SNenv | 25 | Right | $P_s$ | +++ |
| f25L-SNenv | 25 | Left | $P_s$ | +++ |
| parental FPV | NA | NA | NA | − |

[a]Expression of the SNV env gene in infected CEF cells was assayed by indirect immunofluorescence using anti-REV chicken sera, as described in Materials & Methods.

Recombinant fowlpox virus Rec.f29R-SNenv was deposited with the American Type Culture Collection, 12301 Parklawn Drive, Rockville, Md. 20852, USA, under the terms of the Budapest Treaty under accession number VR 2397 on Dec. 17, 1992.

EXAMPLE 3

Southern hybridization analysis

Figure 2:
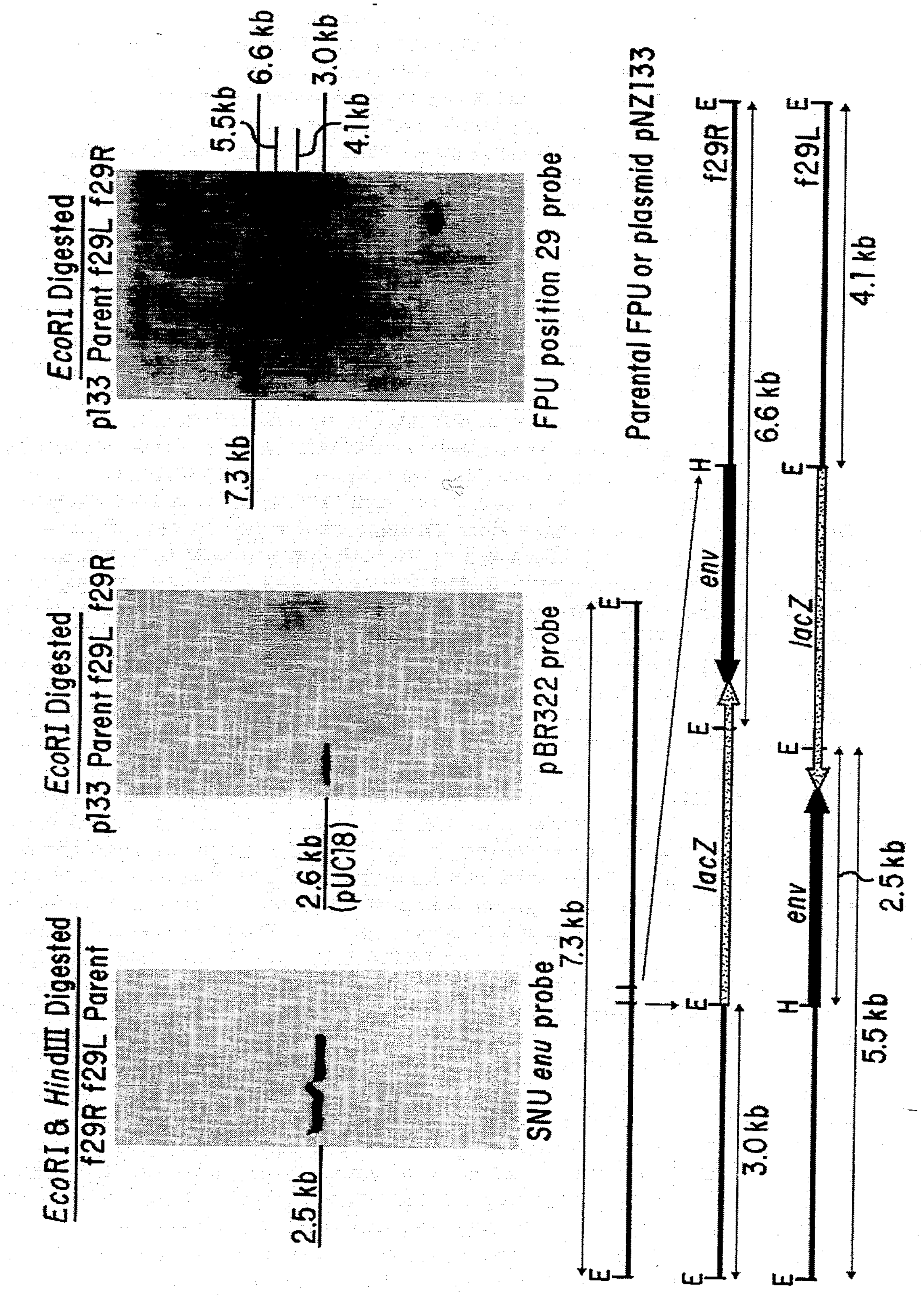
FIG. 2 shows Southern Hybridization analysis of f29R-SNenv and f29L-SNenv genome structure. Total DNA from FPV-infected cells was isolated, digested, and used for southern analysis as described in Materials & Methods. The restriction endonucleases used are shown at the top of each panel, and the digoxigenin-labeled probes are shown at the bottom. Simplified restriction maps, showing EcoRI and HindIII sites for the viruses and plasmids used in the analysis, are shown below the panels. Abbreviations are as follows: f29R, f29R-SNenv; f29L, f29L-SNenv; Parent, parental strain of FPV; p133, plasmid pNZ133 (the entire 7.3 kb EcoRI fragment cloned into pUC18); E, EcoRI site; H, HindIII site.

Total DNA was extracted from CEF infected with recombinant or parental FPV at 4 days post-infection, using proteinase K digestion in the presence of SDS and EDTA, followed by phenol/chloroform extraction and ethanol precipitation (10). After digestion with appropriate restriction enzymes, the DNA was separated on agarose gels and transferred to Zeta-Probe membranes (Bio-Rad, Richmond, Calif.). Labeling of probes and chemiluminescent detection of hybridization signals was performed using the Genius/Lumiphos system (Boehringer Mannheim Biochemicals, Indianapolis, Ind.) according to the manufacture's instructions, except that 3% SDS was used in the pre-hybridization and hybridization solutions. Results are shown in FIG. 2.

EXAMPLE 4

Indirect immunofluorescence

Figure 3:
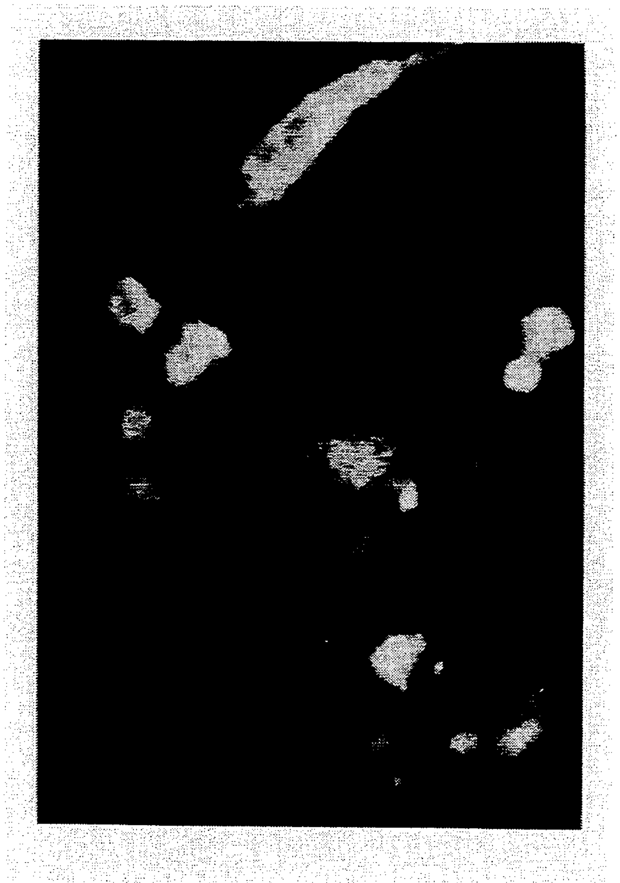
FIG. 3 shows indirect immunofluorescence of recombinant FPV-infected CEF expressing the SNV envelope antigen. Expression of the SNV envelope glycoprotein in CEF cells infected with recombinant FPV f29R-SNenv, detected by indirect immunofluorescence as described in Materials & Methods.

Indirect fluorescent antibody (IFA) assays were performed on recombinant FPV-infected CEF grown on glass coverslips (51). A pool of anti-REV (strain T) sera from convalescent chickens was used as the primary antibody and FITC-conjugated rabbit anti-chicken IgG was used as the secondary antibody. Plaques were visualized using a dark-field microscope with ultraviolet (ploem) illumination, (FIG. 3).

EXAMPLE 5

Radioimmunoprecipitation

[$^{35}$S]-labeled envelope glycoprotein was immunoprecipitated from infected cell lysates with monoclonal antibodies, using a modification of the procedure of Cui et al. (13). CEF monolayers on 60 mm tissue culture plates were infected with recombinant or parental FPV at a multiplicity of 5 PFU/cell, with REV strain SNV or REV-T, or mock infected. FPV and mock infected plates were labeled for 5 h, 20–25 h post-infection. REV-infected cells were labeled for 5 h on the sixth day post-infection. Normal medium was replaced with 2 ml of methionine-free medium 1 h prior to the labeling. Metabolic labeling was with 40 μCi/ml of [$^{35}$S]methionine/[$^{35}$S]cysteine (Tran$^{35}$S-Label™, ICN Biomedicals, Costa Mesa, Calif.). Cells were then washed thoroughly in PBS, scraped and pelleted, and resuspended in 300 μl of lysis buffer (150 mM NaCl/1% Na deoxycholate/1% Triton X-100/0.1% SDS/10 mM Tris-HCl, pH 7.5), and allowed to sit for 30 min at room temperature. Lysates were stored at −20° C. until needed.

Figure 4:
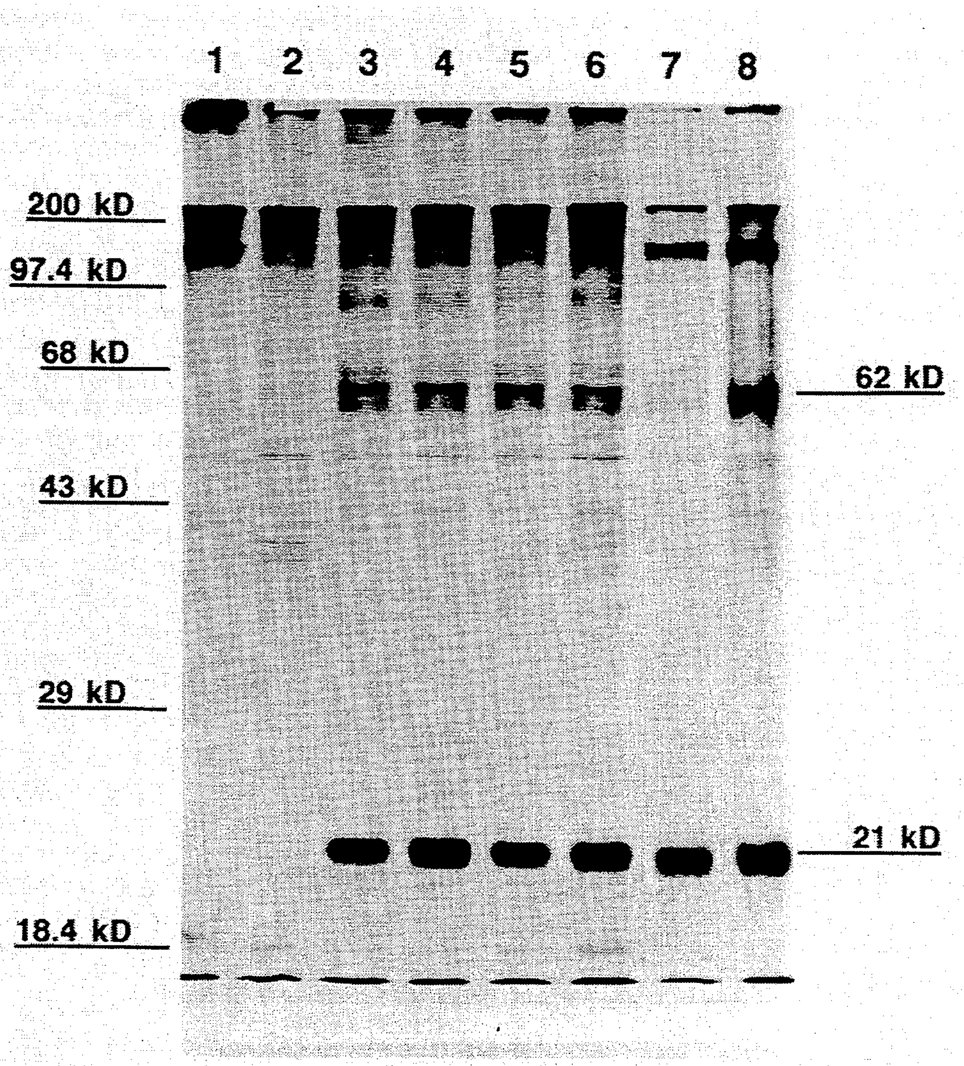
FIG. 4 shows radioimmunoprecipitation of REV envelope glycoproteins. Infected cells were metabolically labeled with [$^{35}$S]methionine, and REV envelope glycoproteins were immunoprecipitated using monoclonal antibody 11A25, as described in Materials & Methods. The following viruses were used: lane 1, mock-infected cells; lane 2, parental FPV; lane 3, f25R-SNenv; lane 4, f25L-SNenv; lane 5, f29L-SNenv; lane 6, f29R-SNenv; lane 7, SNV; lane 8, REV-T(F). The positions of [$^{14}$C]labeled molecular weight markers are shown on the left, and two REV env-related peptides are indicated on the right.

100 μl portions of the lysates were preabsorbed with normal mouse ascites fluid and *Staphylococcus aureus* Cowan I cells (SAC, Boehringer Mannheim Biochemicals, Indianapolis, Ind.). Supernatants were incubated with 2 μl of ascites fluid containing monoclonal antibodies 11A25 or 11B118 (13) and precipitated with SAC. Pellets were then resuspended and boiled in 35 μl of electrophoresis sample buffer, and 20 μl was run on 12% SDS-PAGE gels (24). Following electrophoresis, gels were fixed, impregnated with 22% 2,5-diphenyloxazole in dimethyl sulfoxide, soaked in water, dryed, and exposed to X-ray film (Kodak XAR 5). Results are shown in FIG. 4.

EXAMPLE 6

Production of antibody and virus neutralization assays

RPRL line 0 chicks were immunized intramuscularly at three weeks of age with $10^6$ plaque forming units (PFU) of recombinant or parental FPV in a volume of 0.1 ml. They were boosted twice, at 5 weeks and 6 weeks of age, with a similar dose of virus. Birds were bled 11 days later. Blood samples were allowed to clot, clots were removed by centrifugation, and sera were inactivated for 30 min at 56° C.

Figure 5:
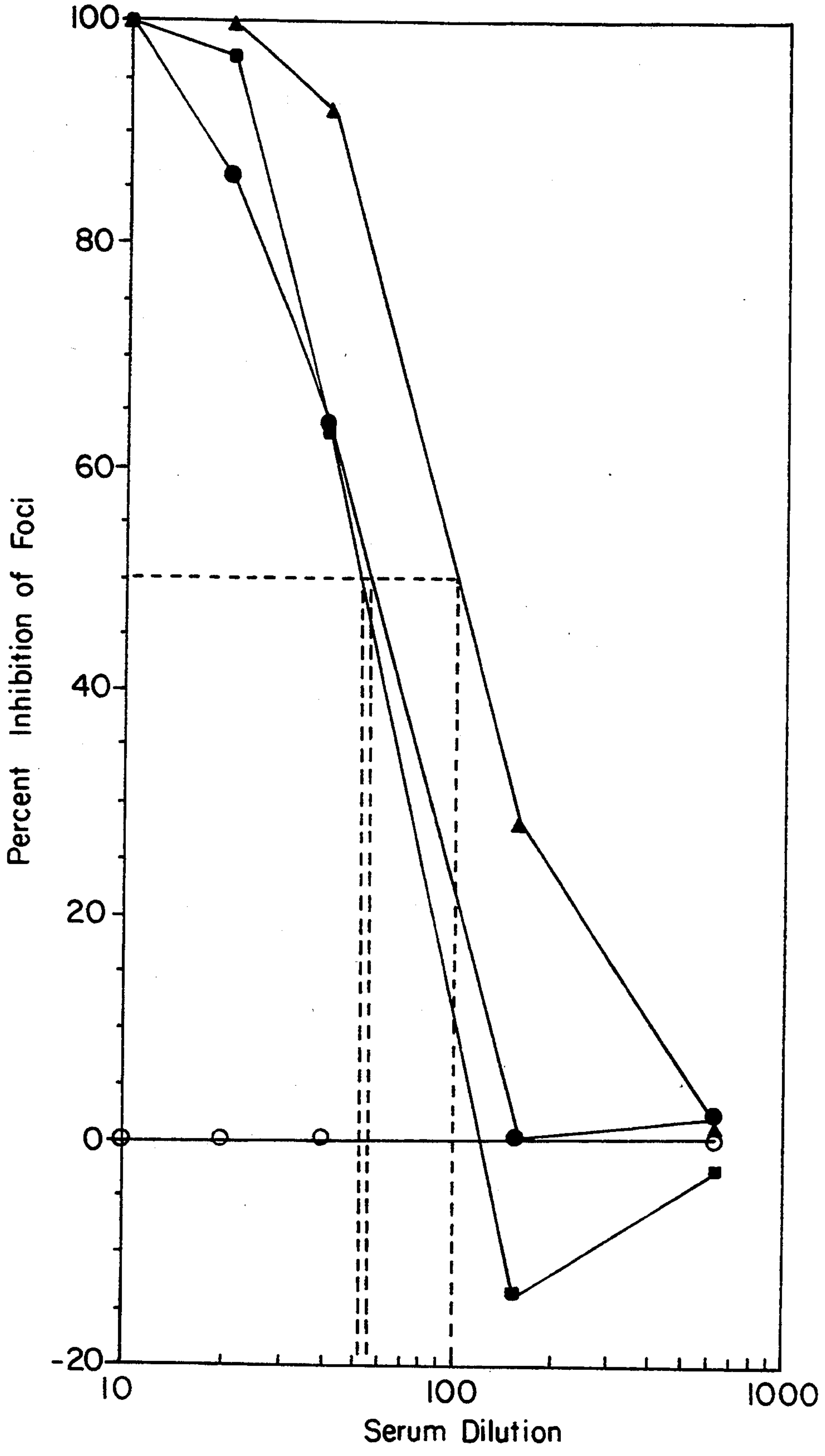
FIG. 5 shows induction of neutralizing antibodies in chickens by recombinant FPVs. Serum pools from vaccinated chickens were assayed for their ability to neutralize SNV infectivity in a foci reduction assay, as described in Materials & Methods. Zero percent inhibition is defined as the number of SNV plaques (approximately 85) obtained using various dilutions of sera from parental FPV-vaccinated birds (○). Other sera were from birds vaccinated with f29R-SNenv (●), f29L-SNenv (■), or f25R-SNenv (▲). Pooled sera were from four or more identically treated birds.

For neutralization assays, sera from similarly treated birds were pooled and appropriate dilutions were made in cell culture medium. 100 focus forming units (FFU) of SNV were added to the dilutions, and neutralization was allowed to proceed for 30 min at room temperature. Virus was then titrated using an indirect immunoperoxidase-based assay which yields macroscopic foci in tissue culture dishes (manuscript in preparation). Briefly, infected CEF monolayers in 60 mm dishes were initially overlaid with 4 ml of 0.6% Bacto agar in medium. After 3 days, 4 ml of liquid medium was added. Three days later, the overlay was removed, monolayer were washed once with PBS, and cells were fixed with a mixture of acetone and ethanol (60:40) for 5–10 min at room temperature. REV foci were subsequently visualized using monoclonal 11A25 (13) as the primary antibody and horseradish peroxidase-conjugated goat anti-mouse IgG (Kirkegaard & Perry Laboratories, Gaithersburg, Md.) as the secondary antibody. Monolayers were washed three times with PBS following each antibody treatment. The substrate solution consisted of freshly prepared 0.6 mg/ml 3,3'-diaminobenzidine tetrahydrochloride (DAB, Eastman Kodak, Rochester, N.Y.), 0.03% $CoCl_2$, and 0.03% $H_2O_2$ in 45 mM Tris-HCl. Foci appeared almost immediately after the addition of substrate (4 ml/dish) and reached maximum intensity after 5–10 min. The neutralizing titer of a serum is defined as the reciprocal of the dilution of the serum which gives 50% inhibition of foci formation (FIG. 5).

Neutralization titers for some serum samples were also determined using an indirect immunofluorescence assay based on limiting dilutions in microtiter plates (12), or using the neutral red-induced plaque assay method of Moscovici et al. (28).

EXAMPLE 7

Protection against SNV challenge

Figure 6A:
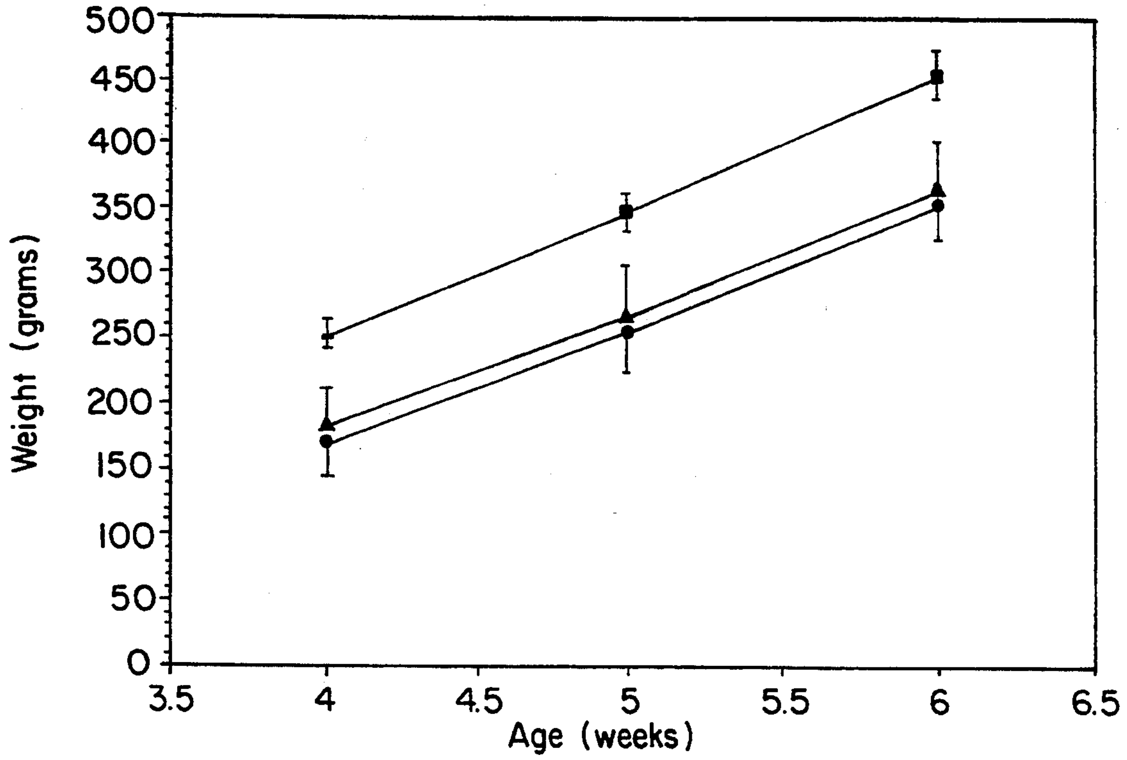
FIGS. 6A and 6B shows weight gain by vaccinated and unvaccinated chickens following challenge with SNV. Birds were vaccinated at one day of age with FPV recombinant f29R-SNenv (■), parental FPV (●), or were left unvaccinated (▲). At 2 weeks of age all birds were challenged with SNV, and they were weighed individually beginning at 4 weeks of age. Male birds are shown in the upper panel (FIG. 6A), and female birds in the lower panel (FIG. 6B). The six groups contained between 6 and 8 chickens each. One standard deviation is indicated by the error bars.
Figure 6B:
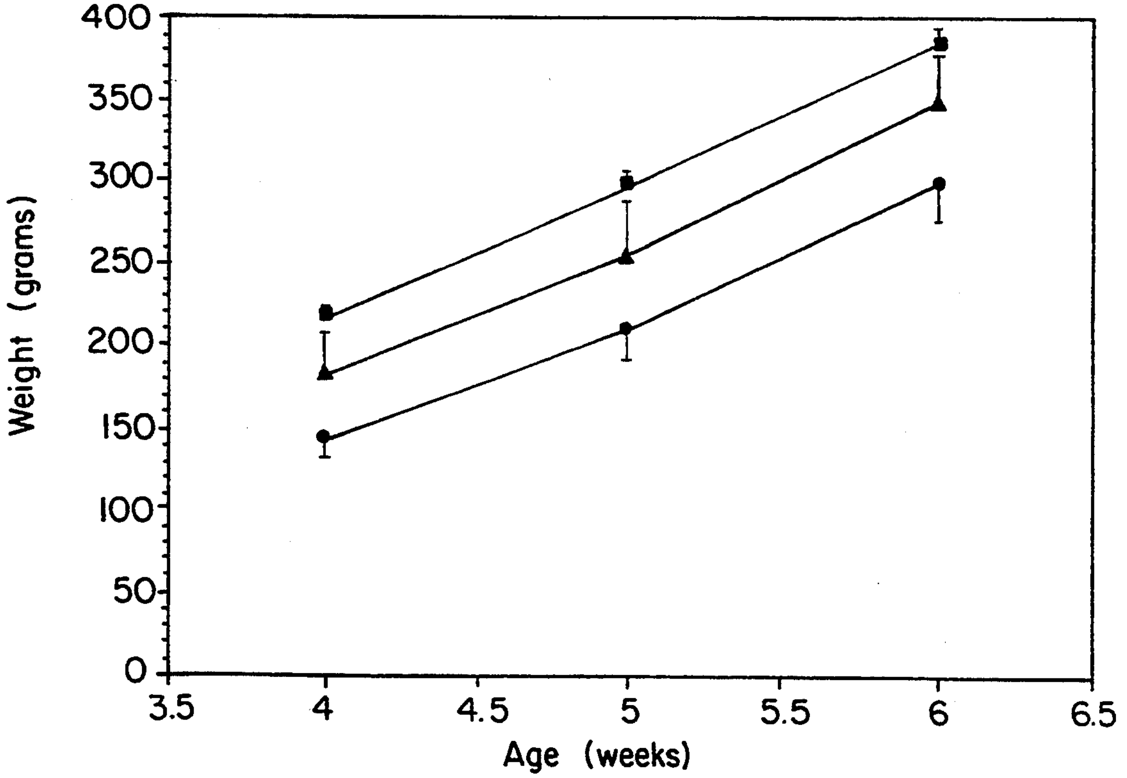

F1 progeny chickens from the cross line 15 $I_5$(males)-×line $7_1$ (females) were immunized intra-abdominally at one day of age with $10^6$ PFU of recombinant f29R-SNenv or parental FPV in a volume of 0.1 ml. At 2 weeks of age they were challenged intra-abdominally with $2\times10^3$ FFU of SNV in 0.1 ml. Birds were bled into heparinized tubes at one week intervals thereafter. Plasmas from individual birds were titrated for viremia and pooled plasma samples were inactivated (30 min at 56° C.) and assayed for neutralizing antibody against SNV using an indirect immunoperoxidase focus assay as described above. In addition, individual birds were weighed at 4 weeks of age (2 weeks post-challenge) and at one week intervals thereafter. Results are shown in FIG. 6.

RESULTS

Generation of stable FPV-SNV recombinants.

Plasmid transfer vectors of the type shown in FIG. 1 were used to recombine a gene casette, consisting of the SNV env gene (SEQ. ID No.:1) and the *E. coli* lacZ gene, into the FPV genome. FPV-infected cell cultures were transfected with plasmid as described in Materials & Methods, and the resulting recombinant FPVs formed blue plaques in the presence of Bluo-gal. The initial frequency of blue recombinant plaques ranged from about 0.01% up to nearly 2% in several experiments. Plaque purification of recombinants was continued until all plaques stained blue with Bluo-gal. This usually took 4 or 5 passages.

In order to test the stability of recombinants, blue plaques from the final round of plaque purification were disrupted by sonication and amplified on CEF monolayers without regard to lacZ phenotype. Two additional blind passages were performed, using a small amount of sonicated lysate as the inoculum for the next passage. The remainder of the lysate from each round was stored at −20° C. until the conclusion of the final passage, when samples from each passage were plaqued and stained with Bluo-gal. The blue-plaque phenotype persisted after three blind passages (at least six generations of virus growth), which is consistent with a stable double crossover-mediated recombination event into a nonessential region of the genome. A few white plaques were seen in some cases, at a frequency of about 1 or 2%, but they did not increase in frequency in subsequent passages. These probably represent point mutations or other small changes in the lacZ gene, rather than a deletion of the lacZ/env casette.

Southern hybridization analysis

Southern analysis was performed on all eight recombinants in order to determine the physical structure of the viral DNA near the insertion sites of the lacZ/env cassette. The results of one such analysis, using recombinants f29R-SNenv and f29L-SNenv, are shown in FIG. 2. The other six recombinants gave similar results. Three probes were employed: 1) a probe to the SNV env gene, which showed this gene to be present in all of the recombinant viruses but not in parental FPV, 2) a probe to plasmid sequences, which showed these sequences to be absent from both recombinant and parental viruses, and 3) a probe to either position 29 or position 25 of the FPV genome, which showed a shift in the number and size of restriction enzyme fragments in the recombinants, relative to parental FPV. These data, taken together, clearly indicate that all recombinants possess the predicted genomic structures. Specifically, they are the result of stable insertions of the lacZ and SNV env genes into the expected positions of the FPV genome, mediated by double crossover recombination events.

Immunofluorescence

Indirect immunofluorescence was used to detect the expression of the SNV env gene (SEQ. ID No.:1) in infected cells, as described in Materials & Methods (Table 1). Low levels of envelope glycoprotein were detected in cells infected with recombinant FPVs which utilized the vaccinia $P_{7.5}$ promoter for expression of the env gene. However, much higher levels of expression were seen when the $P_s$ promoter was used to drive the env gene (FIG. 3).

Radioimmunoprecipitation

Immunoprecipitation of [$^{35}$S]-labeled proteins revealed that all four of the $P_s$-based recombinant FPVs produced significant amounts of SNV envelope glycoprotein (FIG. 4). Two monoclonal antibodies (MAbs) were used. The results with MAb 11A25 are shown in the figure. MAb 11B118 gave virtually identical results. Both of these monoclonals have previously been shown to detect two peptide species, with relative molecular weights of about 62 and 21 kDa, in REV-infected cells (13). The same two peptides were detected in SNV- and REV-T-infected cells in this experiment (6 days post-infection) and also in cells infected with any of the four recombinant FPVs (1 day post-infection), but not in mock-infected or parental FPV-infected cells.

Induction of neutralizing antibody

Three recombinants (f29R-SNenv, f29L-SNenv, and f25R-SNenv) were tested for their ability to induce neutralizing antibodies to the SNV envelope glycoprotein in hyperimmunized chickens. Serum pools from these birds were analyzed for their ability to neutralize SNV in an immunoperoxidase-based focus reduction assay, as described in Materials & Methods. FIG. 5 plots percent neutralization of SNV versus serum dilution. All three recombinants elicited significant levels of neutralizing antibodies to SNV. Titers ranging from about 50 (f29R-SNenv and f29L-SNenv) to about 100 (f25R-SNenv). The difference between the two position 29 recombinants and the position 25 recombinant was not seen in other replicates of this assay.

In a separate experiment; $f_{7.5}$29R-SNenv and $f_{7.5}$29L-SNenv were also tested for their ability to elicit neutralizing antibody (data not shown). These two recombinants, which utilize the $P_{7.5}$ promoter for env expression, gave neutralization titers of about 15 and 20 respectively.

Protection of chickens from SNV challenge

Chickens were vaccinated with FPV recombinant f29R-SNenv or parental FPV at one day of age and challenged with SNV two weeks later. These birds were bled at one week intervals and assayed for viremia and neutralizing antibody. The results are shown in Table 2. Ten of fifteen unvaccinated chickens and twelve of thirteen birds vaccinated with parental FPV were positive for SNV viremia one week post-challenge. Plasma titers in viremic birds averaged $4.6\times10^3$ and $3.3\times10^4$ FFU per ml, respectively. In contrast, SNV was not detected in any of the fifteen chickens that were vaccinated with recombinant f29R-SNenv. By two weeks post-challenge virus had been cleared from all but one bird (this bird was negative for viremia at three weeks post-challenge). One of the viremic chickens in the unvaccinated group died between one and two weeks post-challenge. All of the f29R-SNenv-vaccinated birds remained viremia negative.

Neutralizing antibodies to SNV could not be detected in pools of plasma from unvaccinated or parental FPV-vaccinated chickens at one week post-challenge, when most of these birds were shedding large amounts of virus into the plasma. High titers of neutralizing antibody developed during the next week, and this correlates well with the observed clearing of virus in these birds. Plasma from the recombinant FPV-vaccinated group, in contrast, already contained a moderate level of neutralizing activity by one week post-challenge, which may account for the absence of free virus in these birds. There was no large jump in antibody titer between one and two weeks in these birds, as was seen in the other two groups.

Individual birds were weighed at weekly intervals, beginning at four weeks of age (two weeks post-challenge). At this time, the average weight of the f29R-SNenv-vaccinated birds was 50% greater than that of birds which had received parental FPV. Although the unprotected birds eventually resumed a normal growth rate, they never recoverd from the SNV-induced runting syndrome, remaining nearly 100 grams smaller than the protected group throughout the experiment (FIG. 6).

TABLE 2

Protection of Chickens Vaccinated with f29R-SNenv from SNV Challenge[a]

| Vaccination | Viremia[b] 3 week | Viremia[b] 4 week | Neutralizing Antibody[c] 3 week | Neutralizing Antibody[c] 4 week | Neutralizing Antibody[c] 5 week |
|---|---|---|---|---|---|
| f29R-SNenv | 0/15 | 0/15 | 50 | 90 | 30 |
| Parental FPV | 12/13 ($3.3 \times 10^4$/ml) | 0/13 | <5 | 100 | 200 |
| Unvaccinated | 10/15 ($4.6 \times 10^3$/ml) | 1/14 ($1.1 \times 10^2$/ml) | <5 | 400 | 250 |

[a]Chickens were vaccinated at 1 day of age, challenged at 2 weeks, and bled for viremia and antibody at 3, 4, and 5 weeks of age as described in Materials and Methods.
[b]The ratios of viremic birds to total surviving birds are given. The limit of detection is 2 FFU/ml of plasma. The average plasma titers of those birds which were positive for viremia are given in parentheses.
[c]The neutralizing antibody titers of pooled plasmas were determined using a focus reduction assay, as described in Materials and Methods.

Eight recombinant FPVs were generated, all of which express the envelope glycoprotein of the SNV strain of the avian retrovirus REV. The various recombinants utilized two different nonessential insertion sites in the FPV genome, two different poxviral promoters for env gene expression, and both possible orientations of the foreign gene relative to flanking FPV sequences. The most important determinant in the expression of envelope antigen from these recombinants was the strength of the promoter used to drive expression of the SNV env gene (SEQ. ID. No.:1). $P_{7.5}$ is a naturally occurring late/early promoter of moderate strength which drives expression of the 7.5 kDa polypeptide of vaccinia virus (49). $P_S$ is a synthetic late/early promoter whose sequence is based upon extensive optimization experiments to maximize transcription from early (15) and late (14) vaccinia promoters. The sequence and synthesis of $P_S$ are described elsewhere (56). The recombinants which utilized the $P_S$ promoter expressed much higher levels of envelope glycoprotein than the recombinants which used the $P_{7.5}$ promoter, as determined by immunofluorescent microscopy of infected cells (Table 2). Consistent with this difference is the observation that the $P_S$ recombinants are capable of inducing at least three-fold higher titers of neutralizing antibodies in immunized chickens. Other promoters useful in the present invention include the P11 and H6 promoters of vaccinia virus.

Two nonessential insertion sites within the FPV genome have been used extensively for the generation of recombinant FPVs. These are designated position 25 (35) and 29 (56). Consistent with results reported elsewhere (35), insertion of foreign DNA into position 25 results in recombinants which display a small plaque phenotype, due to disruption of a gene whose product is involved in the release of enveloped virions. Indirect immunofluorescence microscopy of CEF infected with recombinant FPVs showed that the position 29 recombinants may produce levels of envelope antigen which are slightly higher than those produced by the position 25 recombinants (Table 1). In spite of the IFA results and the differences in plaque size, the choice of insertion site made no apparent difference in the amount of antigen expressed in a radioimmunoprecipitation assay (FIG. 4), and a position 25 recombinant was at least as efficient as two position 29 recombinants at eliciting neutralizing antibodies in chickens (FIG. 5).

The orientation of the inserted gene cassette into a nonessential site determines the direction of transcription of the foreign genes relative to flanking FPV genes. Conceivably, strong promoters flanking the insertion site could interfere with (or enhance) transcription of the env or lacZ genes. Conversely, the strong $P_S$ promoter used to drive expression of the env gene could influence the transcription levels of downstream FPV genes, to the detriment of the vector. These effects are possibilities in spite of the efforts taken to minimize them during design of the transfer vectors (head-to-head orientation of the two foreign genes, separated by a bidirectional terminator of early transcription, for example). In the studies reported here, there were no such orientation effects observed, either in terms of the expression levels of envelope glycoprotein or β-galactosidase, or in terms of the growth rate, plaque size, and overall vitality of the FPV vector.

To the extent that it can be determined from the immunoprecipitation data (FIG. 4), post-translational modifications of the envelope glycoprotein in cells infected with the recombinant FPVs seem to be identical to those in REV-infected cells. In both systems, monoclonal antibodies 11A25 and 11B118 precipitate low levels of a 62 kDa, broadly banding polypeptide which probably represents the uncleaved and under glycosylated precursor of both the surface and transmembrane peptides. In addition, higher levels of the 21 kDa mature transmembrane protein were detected in both recombinant FPV- and REV-infected cells.

The ability of these recombinant FPVs to elicit neutralizing antibodies, and to eliminate or greatly reduce the growth of SNV in immunized chickens, suggests that these viruses may be useful as commercial poultry vaccines. Chen et al. (12) compared 26 separate isolates of REV for their ability to induce cross-neutralizing sera in chickens. REVs were originally isolated from turkeys, chickens, ducks, and pheasants, as well as contaminated vaccine and virus stocks. All isolates, including SNV, elicited antisera that were capable of neutralizing all other isolates to a significant degree, with relative neutralizing titer ratios (homologous:heterologous) ranging from 1:1 to 1:16. The implication of this study is that a vaccine which protects well against one strain of REV may protect against many, perhaps all, other strains. Consistent with this thesis is the finding that serum from chickens immunized with three of the SNV envelope-expressing recombinant FPVs reported here are capable of neutralizing not only SNV (FIG. 5), but also REV-T (data not shown).

Although infection of chicken and turkey flocks with REV has been documented frequently (52), most natural infections are subclinical and economic losses due to immunosuppression or lymphoma development are rare. Lymphomas are sporadically seen in turkey flocks, and occasionally can be of considerable economic significance (55). REV-associated disease in chickens is very rare, but outbreaks are currently suspected in the Middle East (53). In addition, lymphomas resulting from REV infection may sometimes be erroneously attributed to lymphoid leukosis or Marek's disease, since differential diagnosis of these three viral diseases is difficult (54). Control procedures for REV infection, other than to insure the absence of REV contamination in biologic products (33), are not available but could become necessary if the disease becomes more prevalent. Vaccination could be an important component of future programs to control losses in commercial flocks and eradicate infection from breeders.

Vaccination against REV could be used either: 1) to stimulate neutralizing antibodies in breeders in order to provide passive protection progeny during the first 2-3 weeks of life, when they are most susceptible to the induction of virus shedding or lymphomas by environmental exposure, or 2) to stimulate immune responses in commercial chickens or turkeys that would protect against immunosuppression and tumor induction resulting from early environmental exposure to REV.

Recombinant FPVs expressing REV genes, as described in this study, can be employed as vaccines against REV-associated diseases in poultry. FPV grows well in turkeys as well as in chickens, and protection of turkey flocks from pox disease has routinely been mediated by vaccine strains of FPV (46). The recombinant FPVs described here are therefore expected to perform well in chickens and turkeys, as well as other bird species such as geese, swans, quail, parrots, and parakeets, etc.

EXAMPLE 8

Preparation of cell-free vaccines

The cell-free vaccine of the present invention can be prepared by a variety of techniques. For example, a cell culture such as a culture of CEF cells in which the recombinant virus of the present invention can grow and replicate is infected with the recombinant virus of the present invention. The cell culture can then be incubated at 37° C. until the virus has had an opportunity to replicate in the cell culture, usually several days. The cells can then be harvested and disrupted by sonication or freeze-thawing according to standard procedures to release the virus into the medium. The cell debris can then be centrifuged to produce a pellet of cell debris at the bottom of the centrifuge tube and a substantially high-titer, cell-free supernatant containing the recombinant virus. The cell-free supernatant, which will consist primarily of the cell culture medium and the recombinant FPV, is then used as a vaccine containing the recombinant virus. In the alternative, the cell-free supernatant is lyophilized to produce a lyophilized vaccine which is reconstituted with a pharmaceutically acceptable carrier such as physiological saline prior to use.

The vaccine of the present invention can be administered to poultry in any manner which allows the recombinant virus in the vaccine to infect the poultry and produce a protective immune response. For example, the vaccine can be applied subcutaneously (s.c.) by scratching the skin or injection with a needle or other implement which contains the virus. The recombinant virus can also be dissolved or suspended in the drinking water of poultry for oral or intranasal administration. The virus may also be mixed with a solid carrier (e.g., poultry feed) for oral administration. Other modes of administration are also contemplated, such as inhalation by use of an aerosol or spray, intramuscular administration, intraperitoneal administration, wing web administration, etc.

A preferred dose for injection appears to be $10^6$ plaque forming units (PFU) per animal in 0.1 ml of a physiologically acceptable liquid carrier. Thus the injectable solution will contain $10^7$ PFU/ml of carrier, usually between $10^3$ to $10^8$ PFU/ml of carrier. The dose and route of administration should be selected to elicit a protective immune response.

In addition to the SNV env glycoprotein discussed above, it is also contemplated in accordance with the present invention that fragments of this gene or variants of this gene which code for variants of this antigen may also be useful as long as the resulting protein (antigen) elicits a protective immune response. It is contemplated that such fragments or variants would code for proteins (antigens) which have substantially the same amino acid sequence as the natural protein, or which elicit a substantially equivalent immune response in the host. The fragments or variants will usually encode a protein which has more than 80%, preferably more than 90%, and more preferably more than 95% homology to the natural protein.

Also contemplated within the scope of the present invention are vaccines comprising recombinant viruses containing multiple REV genes. These include not only the SNV env glycoprotein gene, but REV gag and pol genes as well, for example.

Vaccines of the present invention may also comprise multiple recombinant viruses, each containing a different gene or combination of genes, as listed above.

The recombinant virus of the present invention has the gene for the antigen inserted into the virus under control of appropriate promoters, terminators, etc. so that the virus, after it infects a host cell, can express the protein (antigen), thereby eliciting an immune response in the host. $P_S$, which is a strong synthetic poxvirus promoter which produces high levels of expression during both the early and late stages of infection, is particularly useful. Promoter $P_{7.5}$ is also useful. Other poxvirus promoters, such as the P11 and H6 promoters of vaccinia virus, may also be used.

The invention being thus described it will be obvious that the same may be varied in many ways. Such variations are not to be regarded as a departure from the spirit and scope of the invention, and all such modifications as would be obvious to one skilled in the art are intended to be included within the scope of the following claims.

LITERATURE CITED

1. Bandyopadhyay, P. K. and H. M. Temin. 1984. Expression from an internal AUG codon of herpes simplex thymidine kinase gene inserted in a retrovirus vector. Mol. Cell. Biol. 4:743-748.
2. Barbacid, M., E. Hunter and S. A. Aaronson. 1979. Avian reticuloendotheliosis viruses: evolutionary linkage with mammalian type C retroviruses. J.Virol. 30:508-514.
3. Bayliss, C. D., R. W. Peters, J. K. A. Cook, R. L. Reece, K. Howes, M. M. Binns and M. E. G. Boursnell. 1991. A recombinant fowlpox virus that expresses the VP2 antigen of infectious bursal disease virus induces protection against mortality caused by the virus. Arch. Virol. 120:193-205.
4. Beard, C. W., W. M. Schnitzlein and D. N. Tripathy. 1991. Protection of chickens against highly pathogenic avian influenza virus (H5N2) by recombinant fowlpox viruses. Avian Dis. 35:356–359.

5. Bendheim, U. 1973. A neoplastic disease in turkeys following fowl pox vaccination. Refu. Vet. 30:35–41.
6. Bostock, C. J. 1990. Viruses as vectors. Vet.Microbiol. 23:55–71.
7. Boursnell, M. E. G., P. F. Green, J. I. A. Campbell, A. Deuter, R. W. Peters, F. M. Tomley, A. C. R. Samson, P. Chambers, P. T. Emmerson and M. M. Binns. 1990. Insertion of the fusion gene from Newcastle disease virus into a non-essential region in the terminal repeats of fowlpox virus and demonstration of protective immunity induced by the recombinant. J. Gen. Virol. 71:621–628.
8. Boursnell, M. E. G., P. F. Green, A. C. R. Samson, J. I. A. Campbell, A. Deuter, R. W. Peters, N. S. Millar, P. T. Emmerson and M. M. Binns. 1990. A recombinant fowlpox virus expressing the hemagglutinin-neuraminidase gene of Newcastle disease virus (NDV) protects chickens against challenge by NDV. Virol. 178:297–300.
9. Boyle, D. B. and B. E. H. Coupar. 1988. Construction of recombinant fowlpox viruses as vectors for poultry vaccines. Virus Res. 10:343–356.
10. Carter, J. K. and R. F. Silva. 1990. Cell culture amplification of a defective Marek's disease virus. Virus Genes 4:225–237.
11. Chen, I. S. Y., T. W. Mak, J. J. O'Rear and H. M. Temin. 1981. Characterization of reticuloendotheliosis virus strain T DNA and isolation of a novel variant of reticuloendotheliosis virus strain T by molecular cloning. J.Virol. 48:800–811.
12. Chen, P. Y., Z. Cui, L. F. Lee and R. L. Witter. 1987. Serologic differences among nondefective reticuloendotheliosis viruses. Arch.Virol. 93:233–246.
13. Cui, Z., L. F. Lee, R. F. Silva and R. L. Witter. 1986. Monoclonal antibodies against avian reticuloendotheliosis virus. J.Immunol. 136:4237–4242.
14. Davison, A. J. and B. Moss. 1989. Structure of vaccinia virus late promoters. J. Mol. Biol. 210:771–784.
15. Davison, A. J. and B. Moss. 1989. Structure of vaccinia virus early promoters. J.Mol. Biol. 210:749–769.
16. Dhawale, S., C. E. Beisel and K. Nazerian. 1990. Transient expression assay for qualitative assessment of gene expression by fowlpox virus. Virus Genes 3:213–220.
17. Edbauer, C., R. Weinberg, J. Taylor, A. Reysenelonge, J. F. Bouquet, P. Desmettre and E. Paoletti. 1990. Protection of chickens with a recombinant fowlpox virus expressing the Newcastle disease virus hemagglutinin-neuraminidase gene. Virol. 179:901–904.
18. Goebel, S. J., G. P. Johnson, M. E. Perkus, S. W. Davis, J. P. Winslow and E. Paoletti. 1990. The complete DNA sequence of vaccinia virus. Virol. 179:247–266.
19. Hruby, D. E. 1988. Present and future applications of vaccinia virus as a vector. Vet. Parasit. 29:281–292.
20. Jackson, C. A. W., S. E. Dunn, D. I. Smith, P. T. Gilchrist and P. A. MacQueen. 1977. Proventriculitis, "Nakanuke" and reticuloendotheliosis in chickens following vaccination with herpesvirus of turkeys (HVT). Aust.Vet. J. 53:457–458.
21. Kang, C.-Y. and H. M. Temin. 1973. Lack of sequence homology among RNAs of avian leukosis-sarcoma viruses, reticuloendotheliosis viruses, and chicken endogenous RNA-directed DNA polymerase activity. J.Virol. 12:1314–1324.
22. Kewalramani, V. N., A. T. Panganiban and M. Emerman. 1992. Spleen necrosis virus, an avian immunosuppressive retrovirus, shares a receptor with the type D simian retroviruses. J.Virol. 66:3026–3031.
23. Koo, H. M., J. Gu, A. Varelaechavarria, Y. Ron and J. P. Dougherty. 1992. Reticuloendotheliosis type-C and primate type-D oncoretroviruses are members of the same receptor interference group. J.Virol. 66:3448–3454.
24. Laemmli, U. K. 1970. Cleavage of structural proteins during the assembly of the head of bacteriophage T4. Nature 227:680–685.
25. Letellier, C., A. Burny and G. Meulemans. 1991. Construction of a pigeonpox virus recombinant: expression of the Newcastle disease virus (NDV) fusion glycoprotein and protection of chickens against NDV challenge. Arch.Virol. 118:43–56.
26. Lovinger, G. G., G. Mark, G. J. Todaro and G. Schochetman. 1981. 5'-terminal nucleotide noncoding sequences of retroviruses: relatedness of two old world primate type C viruses and avian spleen necrosis virus. J.Virol. 39:238–245.
27. Mahr, A. and L. G. Payne. 1992. Vaccinia recombinants as vaccine vectors. Immunobiol. 184:126–146.
28. Moscovici, C., D. Chi, L. Gazzolo and M. G. Moscovici. 1976. A study of plaque formation with avian RNA tumor viruses. Virol. 73:181–189.
29. Moss, B. 1990. Regulation of vaccinia virus transcription. Annu. Rev. Biochem. 59:661–688.
30. Moss, B. 1991. Vaccinia virus: a tool for research and vaccine development. Science 252:1662–1667.
31. Nazerian, K., S. Dhawale and W. S. Payne. 1989. Structural proteins of two different plaque-size phenotypes of fowlpox virus. Avian Dis. 33:458–465.
32. Nazerian, K., L. F. Lee, N. Yanagida and R. Ogawa. 1992. Protection against Marek's disease by a fowlpox virus recombinant expressing the glycoprotein B of Marek's disease virus. J.Virol. 66:1409–1413.
33. Nicholas, R. A. J. and D. H. Thornton. 1983. Relative efficiency of techniques for detecting avian reticuloendotheliosis virus as a vaccine contaminant. Res.Vet. Sci. 34:377–379.
34. O'Rear, J. J., S. Mitzutani, G. Hoffman, M. Fiandt and H. M. Temin. 1980. Infectious and noninfectious recombinant clones of the provirus of SNV differ in cellular DNA and are apparently the same in viral DNA. Cell 20:423–430.
35. Ogawa, R., J. G. Calvert, N. Yanagida and K. Nazerian. 1992. Insertional inactivation of a fowlpox virus homologue of the vaccinia virus F12L gene inhibits the release of enveloped virions. J.Gen.Virol. in press.
36. Ogawa, R., N. Yanagida, S. Saeki, S. Saito, S. Ohkawa, H. Gotoh, K. Kodama, K. Kamogawa, K. Sawaguchi and Y. Iritani. 1990. Recombinant fowlpox viruses inducing protective immunity against Newcastle disease and fowlpox viruses. Vaccine 8:486–490.
37. Rice, N. R., T. I. Bonner and R. V. Gilden. 1981. Nucleic acid homology between avian and mammalian type C viruses: relatedness of reticuloendotheliosis virus cDNA to cloned proviral DNA of the endogenous colobus virus CPC-1. Virol. 114:286–290.
38. Schnitzlein, W. M., N. Ghildyal and D. N. Tripathy. 1988. Genomic and antigenic characterization of avipoxviruses. Virus Res. 10:65–76.
39. Solomon, J. J. 1975. Preparation of avian cell cultures. Tissue Culture Assoc. 1:7–11.

40. Tartaglia, J., S. Pincus and E. Paoletti. 1990. Poxvirus-based vectors as vaccine candidates. Crit. Rev. Immun. 10:13–30.

41. Taylor, J., C. Edbauer, A. Rey-Senelonge, J-F. Bouquet, E. Norton, S. J. Goebel, P. Desmettre and E. Paoletti. 1990. Newcastle disease virus fusion protein expressed in a fowlpox virus recombinant confers protection in chickens. J.Virol. 64: 1441–1450.

42. Taylor, J. and E. Paoletti. 1988. Fowlpox virus as a vector in non-avian species. Vaccine 6:466–468.

43. Taylor, J., C. Trimarchi, R. Weinberg, B. Languet, F. Guillemin, P. Desmettre and E. Paoletti. 1991. Efficacy studies on a canarypox-rabies recombinant virus. Vaccine 9:190–193.

44. Taylor, J., R. Weinberg, Y. Kawaoka, R. G. Webster and E. Paoletti. 1988. Protective immunity against avian influenza induced by a fowlpox virus recombinant. Vaccine 6:504–508.

45. Taylor, J., R. Weinberg, J. Tartaglia, C. Richardson, G. Alkhatib, D. Briedis, M. Appel, E. Norton and E. Paoletti. 1992. Nonreplicating viral vectors as potential vaccines: recombinant canarypox virus expressing measles virus fusion (F) and hemagglutinin (HA) glycoproteins. Virol. 187:321–328.

46. Tripathy, D. N. 1991. Pox, p. 583–596. In B. W. Calnek, H. J. Barnes, C. W. Beard, W. M. Reid and H. W. Yoder,Jr. (ed.), Diseases of Poultry, 9th ed. Iowa State University Press, Ames, Iowa.

47. Tsai, W.-P., T. D. Copeland and S. Oroszlan. 1985. Purification and chemical and immunological characterization of avian reticuloendotheliosis virus gag-gene-encoded structural proteins. Virol. 140:289–312.

48. Tsai, W.-P., T. D. Copeland and S. Oroszlan. 1986. Biosynthesis and chemical and immunological characterization of avian reticuloendotheliosis virus env gene-encoded proteins. Virol. 155:567–583.

49. Venkatesan, S., B. M. Baroudy and B. Moss. 1981. Distinctive nucleotide sequences adjacent to multiple initiation and termination sites of an early vaccinia virus gene. Cell 25:805–813.

50. Wild, F., P. Giraudon, D. Spehner, R. Drillien and J. P. Lecocq. 1990. Fowlpox virus recombinant encoding the measles virus fusion protein: protection of mice against fatal measles encephalitis. Vaccine 8:441–442.

51. Witter, R. L. 1989. Reticuloendotheliosis, p. 143–148. In H. G. Purchase, L. H. Arp, C. H. Domermuth and J. E. Pearson (ed.), A Laboratory Manual for the Isolation and Identification of Avian Pathogens, 3rd ed. Kendall/Hunt Publishing Company, Dubuque, Iowa.

52. Witter, R. L. 1991. Reticuloendotheliosis, p. 439–456. In B. W. Calnek, H. J. Barnes, C. W. Beard, W. M. Reid and H. W. Yoder,Jr. (ed.), Diseases of Poultry, 9th ed. Iowa State University Press, Ames, Iowa.

53. Witter, R. L. 1991. Reticuloendotheliosis virus: new findings and impact on industry, p. 22–25. In Avian Tumor Virus Symposium, American Association of Avian Pathologists/American Veterinary Medical Associati, Seattle, Wash.

54. Witter, R. L. 1991. Differential diagnosis of lymphoid tumors, p. 52–55. In Avian Tumor Virus Symposium, American Association of Avian Pathologists/American Veterinary Medical Associati, Seattle, Wash.

55. Witter, R. L. and D. W. Salter. 1989. Vertical transmission of reticuloendotheliosis virus in breeder turkeys. Avian Dis. 33:226–235.

56. Yanagida, N., R. Ogawa, Y. Li, L. F. Lee and K. Nazerian. 1992. Recombinant fowlpox viruses expressing the glycoprotein B homolog and the pp38 gene of Marek's disease virus. J.Virol. 66:1402–1408.

57. Yuasa, N., I. Yoshida and T. Taniguchi. 1976. Isolation of a reticuloendotheliosis virus from chickens inoculated with Marek's disease vaccine. Nat. Inst. Anim. Health Q. 16:141–151.

What is claimed is:

1. An Avipoxvirus that expresses a gene encoding an envelope glycoprotein of spleen necrosis virus.

2. The Avipoxvirus of claim 1, where said Avipoxvirus is a fowlpox virus.

3. The Avipoxvirus of claim 1, wherein said gene encodes the envelope glycoprotein of the spleen necrosis virus strain of reticuloendotheliosis virus (SE ID No.:2).

4. The Avipoxyvirus of claim 1, wherein said gene is under the control of a natural or synthetic promoter.

5. The Avipoxvirus of claim 4, where said promoter is a poxviral promoter.

6. The Avipoxvirus of claim 4, wherein said natural promoter is the $P_{7.5}$ promoter of vaccinia virus.

7. The Avipoxvirus of claim 4, wherein said synthetic promoter is the $P_S$ promoter.

8. The Avipoxvirus of claim 1, wherein said gene is inserted into a nonessential region in the genome of said Avipoxvirus.

9. The Avipoxvirus of claim 8, wherein said nonessential region is position 25 or position 29 in the genome of said Avipoxvirus.

10. The Avipoxvirus of claim 1, wherein said gene is inserted in either of both possible orientations relative to flanking sequences of said Avipoxvirus.

11. The Avipoxvirus of claim 1, wherein said Avipoxvirus is a fowlpox virus, said gene encodes an envelope glycoprotein, said avian retrovirus is the spleen necrosis virus strain of arian reticuloendotheliosis virus, and wherein said gene is inserted in either of both possible orientations relative to flanking Avipoxvirus sequences into either position 25 or position 29 of the genome of said Avipoxvirus.

12. A vaccine composition, comprising:
an anti-avian retrovirus effective amount of said Avipoxvirus of claim 1; and
a pharmaceutically acceptable carrier.

13. A vaccine composition, comprising:
an anti-avian retrovirus effective amount of said Avipoxvirus of claim 11, and
a pharmaceutically acceptable carrier.

14. A method for immunizing poultry against avian reticuloendotheliosis retrovirus-associated diseases, comprising administering to said poultry said vaccine of claim 13.

15. A method for producing passive protection against avian reticuloendotheliosis retrovirus-associated diseases in poultry progeny, comprising administering to poultry breeder stock said vaccine of claim 13, resulting in passive protection in said poultry progeny during the first weeks of life.

16. The method of claim 14, wherein said poultry is a member selected from the group consisting of a chicken, a duck, and a turkey, and said administering is conducted orally or subcutaneously.

17. The method of claim 13, wherein said poultry is a member selected from the group consisting of a chicken, a duck, and a turkey, and said administering is conducted orally or subcutaneously.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 1704 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

```
ATGGACTGTC TCACCAACCT CCGATCCGCT GAGGGTAAAG TTGACCAGGC GAGCAAAATC    60

CTAATTCTCC TTGTGGCTTG GTGGGGGTTT GGGACCACTG CCGAAGGTTA CCCCTTGCAG   120

CAACTTTGGG AACTGCCTTG TGACTGTTCC GGGGGATATG TCTCCTCCAT ACCTACCTAT   180

TACACCTACT CCCTCGATTG TGGTGGCTCC ACCGCCTACC TGACTTACGG ATCTGGTACA   240

GGGAGTTGGA GCTGGGGAGG GGGATTTAAA CAACAGTGGG AATGTGTGTT TAAACCTAAG   300
```

-continued

```
ATCATACCCT CTGTGCAGGG GCAGCCAGGG CCCTGCCCAT CTGAATGCCT CCAGATAGCT  360
ACTCAAATGC ATTCCACTTG TTATGAAAAG ACTCAGGAAT GCACCCTCCT GGGAAAAACC  420
TATTTTACTG CCATCCTACA GAAAACAAAG CTAGGCTCGT ATGAAGACGG GCCTAATAAA  480
CTGATCCAGG CCTCTTGCAC GGGAACCGTA GGGAAACCAG TATGTTGGGA CCCTGTAGCC  540
CCTGTGTATG TCTCTGATGG CGGCGGTCCC ACTGACATGA TTCGGGAAGA GTCTGTGCGT  600
GAAAGACTAG AGGAAATCAT CAGGCACAGC TACCCCTCCG TACAGTATCA CCCTTTAGCC  660
CTGCCCCGAT CAAGAGGAGT AGATCTGGAT CCCCAGACGT CTGACATACT GGAAGCTACT  720
CACCAGGTCC TTAATGCCAC TAATCCCAAG CTAGCAGAGA ACTGCTGGCT TTGTATGACT  780
CTTGGAACTC CAATCCCCGC AGCCATCCCG ACGAATGGCA ATGTCACTCT CGATGGAAAT  840
TGCAGTCTTA GCCTCCCTTT CGGGTGCAAC CCACCTGGGT CAATAGATGT CAGCTGCTAT  900
GCAGGGGAAG CAGACAATAG GACTGGTATA CCCGTAGGGT ATGTCCATTT TACTAACTGC  960
ACTAGTATCC AGGAGGTCAC TAATGAGACA AGTCAAATGG GAAATCTTAC GAGGCTATGT 1020
CCTCCACCAG GTCATGTATT TGTGTGTGGG AACAACATGG CCTACACGGC ACTCCCTAAT 1080
AAATGGATAG GGCTGTGCAT ACTGGCATCA ATCGTACCCG ACATAAGCAT AATATCCGGG 1140
GAAGAGCCTA TCCCACTCCC ATCCATCGAG TACACCGCTA GGCGTCATAA GAGGGCAGTC 1200
CAGTTTATCC CCCTGCTTGT GGGTCTAGGG ATTTCAGGGG CTACACTTGC TGGTGGAACG 1260
GGGCTTGGGG TCTCCGTTCA CACTTATCAC AAGCTCTCTA ATCAATTGAT TGAAGATGTC 1320
CAGGCTCTTT CAGGGACCAT CAATGACCTA CAGGACCAGA TTGACTCCCT GGCTGAGGTT 1380
GTCTTACAAA ATAGAAGAGG GTTAGACCTA TTGACTGCCG AACAAGGAGG AATATGTCTC 1440
GCACTCCAGG AGAAGTGTTG TTTTTACGCT AACAAGTCGG GTATCGTACG TGACAAGATC 1500
CGAAAACTCC AAGAGGACCT TATCGAGAGA AAACGTGCAC TGTACGACAA CCCCCTGTGG 1560
AGCGGCTTGA ACGGCTTCCT TCCATATTTG CTACCCTTGT TAGGCCCCCT GTTTGGGCTC 1620
ATATTGTTCC TGACCCTCGG CCCGTGCATT ATGAAGACCC TGACTCGCAT TATACATGAC 1680
AAAATTCAGG CAGTAAAATC CTAG                                        1704
```

( 2 ) INFORMATION FOR SEQ ID NO:2:

( i ) SEQUENCE CHARACTERISTICS:
( A ) LENGTH: 567 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:2:

```
Met Asp Cys Leu Thr Asn Leu Arg Ser Ala Glu Gly Lys Val Asp Gln
1               5                   10                  15
Ala Ser Lys Ile Leu Ile Leu Leu Val Ala Trp Trp Gly Phe Gly Thr
            20                  25                  30
Thr Ala Glu Gly Tyr Pro Leu Gln Gln Leu Trp Glu Leu Pro Cys Asp
        35                  40                  45
Cys Ser Gly Gly Tyr Val Ser Ser Ile Pro Thr Tyr Tyr Thr Tyr Ser
    50                  55                  60
Leu Asp Cys Gly Gly Ser Thr Ala Tyr Leu Thr Tyr Gly Ser Gly Thr
65                  70                  75                  80
Gly Ser Trp Ser Trp Gly Gly Gly Phe Lys Gln Gln Trp Glu Cys Val
                85                  90                  95
```

-continued

Phe Lys Pro Lys Ile Ile Pro Ser Val Gln Gly Gln Pro Gly Pro Cys
100 105 110

Pro Ser Glu Cys Leu Gln Ile Ala Thr Gln Met His Ser Thr Cys Tyr
115 120 125

Glu Lys Thr Gln Glu Cys Thr Leu Leu Gly Lys Thr Tyr Phe Thr Ala
130 135 140

Ile Leu Gln Lys Thr Lys Leu Gly Ser Tyr Glu Asp Gly Pro Asn Lys
145 150 155 160

Leu Ile Gln Ala Ser Cys Thr Gly Thr Val Gly Lys Pro Val Cys Trp
165 170 175

Asp Pro Val Ala Pro Val Tyr Val Ser Asp Gly Gly Gly Pro Thr Asp
180 185 190

Arg Met Ile Arg Glu Glu Ser Val Arg Glu Arg Leu Glu Glu Ile Ile
195 200 205

His Ser Tyr Pro Ser Val Gln Tyr His Pro Leu Ala Leu Pro Arg Ser
210 215 220

Arg Gly Val Asp Leu Asp Pro Gln Thr Ser Asp Ile Leu Glu Ala Thr
225 230 235 240

His Gln Val Leu Asn Ala Thr Asn Pro Lys Leu Ala Glu Asn Cys Trp
245 250 255

Leu Cys Met Thr Leu Gly Thr Pro Ile Pro Ala Ala Ile Pro Thr Asn
260 265 270

Gly Asn Val Thr Leu Asp Gly Asn Cys Ser Leu Ser Leu Pro Phe Gly
275 280 285

Cys Asn Pro Pro Gly Ser Ile Asp Val Ser Cys Tyr Ala Gly Glu Ala
290 295 300

Asp Asn Arg Thr Gly Ile Pro Val Gly Tyr Val His Phe Thr Asn Cys
305 310 315 320

Thr Ser Ile Gln Glu Val Thr Asn Glu Thr Ser Gln Met Gly Asn Leu
325 330 335

Thr Arg Leu Cys Pro Pro Pro Gly His Val Phe Val Cys Gly Asn Asn
340 345 350

Met Ala Tyr Thr Ala Leu Pro Asn Lys Trp Ile Gly Leu Cys Ile Leu
355 360 365

Ala Ser Ile Val Pro Asp Ile Ser Ile Ile Ser Gly Glu Glu Pro Ile
370 375 380

Pro Leu Pro Ser Ile Glu Tyr Thr Ala Arg Arg His Lys Arg Ala Val
385 390 395 400

Gln Phe Ile Pro Leu Leu Val Gly Leu Gly Ile Ser Gly Ala Thr Leu
405 410 415

Ala Gly Gly Thr Gly Leu Gly Val Ser Val His Thr Tyr His Lys Leu
420 425 430

Ser Asn Gln Leu Ile Glu Asp Val Gln Ala Leu Ser Gly Thr Ile Asn
435 440 445

Asp Leu Gln Asp Gln Ile Asp Ser Leu Ala Glu Val Val Leu Gln Asn
450 455 460

Arg Arg Gly Leu Asp Leu Leu Thr Ala Glu Gln Gly Gly Ile Cys Leu
465 470 475 480

Ala Leu Gln Glu Lys Cys Cys Phe Tyr Ala Asn Lys Ser Gly Ile Val
485 490 495

Arg Asp Lys Ile Arg Lys Leu Gln Glu Asp Leu Ile Glu Arg Lys Arg
500 505 510

Ala Leu Tyr Asp Asn Pro Leu Trp Ser Gly Leu Asn Gly Phe Leu Pro

-continued

| | | | | | | | | | | | | | | | |
|---|---|---|---|---|---|---|---|---|---|---|---|---|---|---|---|
| | | 515 | | | | | 520 | | | | | 525 | | | |
| Tyr | Leu | Leu | Pro | Leu | Leu | Gly | Pro | Leu | Phe | Gly | Leu | Ile | Leu | Phe | Leu |
| | 530 | | | | | 535 | | | | | 540 | | | | |
| Thr | Leu | Gly | Pro | Cys | Ile | Met | Lys | Thr | Leu | Thr | Arg | Ile | Ile | His | Asp |
| | 545 | | | | | 550 | | | | | 555 | | | | 560 |
| Lys | Ile | Gln | Ala | Val | Lys | Ser | | | | | | | | | |
| | | | | 565 | | | | | | | | | | | |